United States Patent
Amakawa et al.

(10) Patent No.: US 8,119,556 B2
(45) Date of Patent: Feb. 21, 2012

(54) PRODUCTION METHOD OF PRIMARY AMINES AND CATALYSTS FOR PRODUCING PRIMARY AMINES

(75) Inventors: Kazuhiko Amakawa, Niigata (JP); Yoshiaki Yamamoto, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 12/836,437

(22) Filed: Jul. 14, 2010

(65) Prior Publication Data

US 2010/0279857 A1    Nov. 4, 2010

Related U.S. Application Data

(62) Division of application No. 11/836,224, filed on Aug. 9, 2007, now Pat. No. 7,767,859.

(30) Foreign Application Priority Data

Aug. 9, 2006  (JP) .................... 2006-216940

(51) Int. Cl.
*B01J 21/18* (2006.01)
*B01J 23/755* (2006.01)
*B01J 23/75* (2006.01)
*B01J 23/745* (2006.01)

(52) U.S. Cl. ........ 502/184; 502/301; 502/325; 502/333; 502/338

(58) Field of Classification Search .................. 502/301, 502/325, 333, 338, 184
See application file for complete search history.

(56) References Cited

U.S. PATENT DOCUMENTS

| 2,756,243 | A | * | 7/1956 | Umhoefer | ...................... 552/265 |
| 2,941,954 | A |   | 6/1960 | Wilkes |   |
| 3,573,038 | A | * | 3/1971 | Jung et al. | ...................... 502/301 |
| 5,986,127 | A |   | 11/1999 | Ionkin et al. |   |
| 7,419,928 | B2 | * | 9/2008 | Malek et al. | ...................... 502/20 |

FOREIGN PATENT DOCUMENTS

| CA | 2250770 | 8/1998 |
| EP | 1108469 A1 | 6/2001 |
| WO | WO 98/33767 | 8/1998 |
| WO | WO 2006/050749 A1 | 5/2006 |
| WO | WO 2006/062496 A1 | 6/2006 |

OTHER PUBLICATIONS

Extended European Search Report for Application No. EP07113901. 8-2104, dated Feb. 5, 2008.
XP-002143882, Derwent Publications, vol. 1997, No. 16, 1997 (Abstract of JP 19950197692).

* cited by examiner

*Primary Examiner* — Elizabeth Wood
(74) *Attorney, Agent, or Firm* — Antonelli, Terry, Stout & Kraus, LLP.

(57) ABSTRACT

A method of producing a primary amine by the hydrogenation of a nitrile in the presence of a hydrogenation catalyst. The hydrogenation catalyst contains at least one metal selected from the group consisting of nickel, cobalt and iron. Before use in the hydrogenation of nitrile, the hydrogenation catalyst is pretreated with at least one treating agent selected from the group consisting of hydrocarbons, alcohols, ethers, esters and carbon monoxide at 150 to 500° C.

11 Claims, No Drawings

PRODUCTION METHOD OF PRIMARY AMINES AND CATALYSTS FOR PRODUCING PRIMARY AMINES

This application is a Divisional application of prior application Ser. No. 11/836,224, filed Aug. 9, 2007, now U.S. Pat. No. 7,767,859, issued Aug. 3, 2010, the contents of which application are incorporated herein by reference in their entirety.

BACKGROUND OF THE INVENTION

1. Field of the Invention

The present invention relates to a production method of primary amines by the catalytic hydrogenation of nitriles and a catalyst for use in the production.

2. Description of the Prior Art

The production of primary amines by the hydrogenation of nitriles in the presence of a hydrogenation catalyst containing a metal selected from nickel, cobalt and iron have been well known. In the production of primary amines by the hydrogenation of nitrile, condensation products such as secondary and tertiary amines are by-produced by the intermolecular condensation, to reduce the yield of primary amines (Handbook of Heterogeneous Catalytic Hydrogenation for Organic Synthesis, Shigeo Nishimura, John Wiley & Sons, Inc., Chapter 7 Hydrogenation of Nitriles p 254-285).

To prevent the by-production of secondary and tertiary amines by the condensation, a method where the hydrogenation is conducted in ammonia solvent (JP 53-20969B, JP 8-299799A, JP 2002-505192A and JP 51-6971A) and a method where the hydrogenation is conducted in the presence of a hydroxide of an alkali metal or alkaline earth metal (JP 7-518900A, JP 7-517801A, JP 38-8719B and JP 54-41804A) have been hitherto well known. However, the use of ammonia solvent requires a pressure-resistant apparatus because of a high vapor pressure of ammonia. The industrial use of alkali metal involves a difficulty in the treatment of waste liquid containing alkali metal. In addition, these method are difficult to completely prevent the side reaction. Therefore, the improvement is still required.

To prevent the side reaction thereby to increase the yield, there have been proposed a method to modify the catalyst with formaldehyde, etc. in a liquid dispersion medium (JP 2001-212461A), a method of carrying out the hydrogenation in the co-presence of a cyanate (JP 2001-302595A), and a method of carrying out the hydrogenation in the presence of an alkali carbonate-modified catalyst which is prepared by treating the catalyst in an aqueous solution of alkali carbonate (US 2005/0159624A). These methods are reported to be used in combination with the hydrogenation in ammonia solvent or the hydrogenation in the co-presence of an alkali metal or alkaline earth metal, and proved to improve the yield in some extent. However, the method of modifying the catalyst with formaldehyde and the method of using the alkali carbonate-modified catalyst need an additional step of pretreating the catalyst in an aqueous solution. If the hydrogenation is conducted in a non-aqueous solvent, the water should be removed from the catalyst by repeated solvent exchange operation, to complicate the process. The method of using the cyanate is not industrially advantageous because the cyanate is an expensive and special chemical. In JP 40-10133B and Japanese Patent 2937083, a method of selectively hydrogenating one of two nitrile groups in the presence of a catalyst pretreated with carbon monoxide, etc. is proposed. However, these patent documents address or consider nothing about the reduction of yield in the hydrogenation of nitriles which is caused by the side reaction. In addition, these patent documents are completely silent about the hydrogenation of two nitrile groups and address or consider nothing about the problems involved in the hydrogenation of two nitrile groups.

In any of the known methods, it is difficult to completely prevent the side reaction which by-produces the condensation products. Therefore, it is keenly required to develop an improved method which is capable of preventing the side reaction to increase the yields.

SUMMARY OF THE INVENTION

An object of the present invention is to solve the above problems in prior art and provide a method of producing primary amines from nitriles in high yields while preventing the side reaction which gives the condensation products.

As a result of extensive research, the inventors have found that the above object is achieved by pretreating the catalyst for hydrogenating nitriles with hydrocarbon compound, etc. before use in the hydrogenation. The present invention is based on this finding.

Thus, the present invention relates to a method of producing a primary amine, which includes a step of pretreating a hydrogenation catalyst containing at least one metal selected from the group consisting of nickel, cobalt and iron with at least one treating agent selected from the group consisting of hydrocarbons, natural gas, alcohols, ethers, esters and carbon monoxide at 150 to 500° C., thereby obtaining a pretreated hydrogenation catalyst; and a step of reacting a nitrile with hydrogen in the presence of the pretreated hydrogenation catalyst.

The present invention further relates to a catalyst for producing a primary amine by a hydrogenation of nitrile, which contains at least one metal selected from the group consisting of nickel, cobalt and iron, and which is modified by a pretreatment with at least one treating agent selected from the group consisting of hydrocarbons, natural gas, alcohols, ethers, esters and carbon monoxide at 150 to 500° C.

DETAILED DESCRIPTION OF THE INVENTION

In the present invention, the primary amine is produced by the reaction of nitrile with hydrogen in the presence of a catalyst. Any of aliphatic nitriles, alicyclic nitriles and aromatic nitriles may be used as the raw nitrile. The raw nitrile may have two or more nitrile groups. In addition to the nitrile group, the raw nitrile may have one or more functional groups such as amino group, halogen group, alkyl group, phenyl group, hydroxyl group, ester group, and ether group. Further, the raw nitrile may have one or more functional groups which are capable of being hydrogenated such as ketone group and imino group. These functional groups may be hydrogenated into hydroxyl group or amino group simultaneously with the hydrogenation of nitrile group. Examples of the aliphatic nitriles include acetonitrile, propiononitrile, butanenitrile, pentanenitrile, hexanenitrile, heptanenitrile, octanenitrile, butanedinitrile (adiponitrile), pentanedinitrile, hexanedinitrile, heptanedinitrile, octanedinitrile, and benzyl cyanide.

Examples of the alicyclic nitriles include cyclohexanenitrile, cyclohexanedinitrile, 3-cyano-3,5,5-trimethylcyclohexanone, 3-cyano-3,5,5-trimethylcyclohexylimine, and tricyclodecanedicarbonitrile.

Examples of the aromatic nitriles include benzonitrile, methylbenzonitrile, dicyanobenzene, tricyanobenzene, biphenylnitrile, cyanonaphthalene, and dicyanonaphthalene.

In addition, heterocyclic nitriles such as pyridinecarbonitrile and pyrimidinecarbonitrile may be used as the raw nitrile.

The present invention is preferably applicable to the production of aromatic ring-containing diamines by the hydrogenation of aromatic nitriles, particularly, the production of xylylenediamine by the hydrogenation of dicyanobenzenes. The dicyanobenzenes are hydrogenated respectively into corresponding primary amines. Although the present invention is particularly suitable to the production of diamines by the hydrogenation of both cyano groups, the present invention may be also applicable to the production of aminonitrile in which one of the nitrile groups of dinitrile is hydrogenated into amino group, for example, the production of aminocapronitrile by the hydrogenation of adiponitrile and the production of cyanobenzylamine by the hydrogenation of dicyanobenzene.

Although the hydrogenation may be conducted in either gas phase (vapor phase) or liquid phase, the hydrogenation is generally conducted in liquid phase in many cases except for the hydrogenation of a nitrile having a low boiling point such as acetonitrile. The hydrogenation in liquid phase can be conducted in a reaction solvent. Many solvents which are stable under the hydrogenation conditions are usable as the reaction solvent. Examples thereof include hydrocarbon solvents such as toluene, xylene and trimethylbenzene; ether solvents such as tetrahydrofuran and dioxane; lower aliphatic amide solvents such as dimethylformamide, dimethylacetamide and N-methylpyrrolidone; alcohol solvents such as methanol, ethanol and propanol; and ammonia. These solvents may be used alone or in combination of two or more. Since the yield of the primary amine is increased, it is preferable to use ammonia as a part of the reaction solvent, for example, 2 to 100% by weight of the reaction solvent. The amount of the reaction solvent to be used depends upon the kinds of nitrile and catalyst, and preferably from 0.5 to 99 parts by weight, more preferably from 1 to 98 parts by weight, and still more preferably from 1 to 30 parts by weight, each based on 1 part by weight of nitrile.

The hydrogen gas for use in the hydrogenation of nitrile may contain impurities, such as methane and nitrogen, which are inert to the hydrogenation. However, to ensure a sufficient hydrogen partial pressure, a higher total reaction pressure is required if the content of impurities is high, thereby making the process industrially disadvantageous. Therefore, the gas having a hydrogen content of 50 mol % or more is preferably used.

In the present invention, the primary amine is produced by the reaction of nitrile and hydrogen in the presence of a hydrogenation catalyst. The hydrogenation catalyst used in the present invention contains, as the active metal component, at least one metal selected from the group consisting of nickel, cobalt and iron, with the catalyst containing nickel and/or cobalt being preferred and the catalyst containing nickel being particularly preferred. The form of catalyst may be a supported catalyst (US 2002-177735A), a non-supported metal catalyst (JP 8-299799A and JP 2002-505192A), or a sponge metal catalyst (Raney nickel, Raney cobalt, etc.). The content of the active metal component in the supported catalyst is preferably from 10 to 98% by weight, more preferably from 20 to 90% by weight, and still more preferably from 30 to 80% by weight. Examples of the carrier for the supported catalyst include alumina, silica, diatomaceous earth, silica-alumina, magnesia, titania, zirconia, silica-zirconia, and carbon. The catalyst may be modified by the addition of at least one component selected from the group consisting of alkali metals (Li, Na, K, Rb, Cs), alkaline earth metals (Mg, Ca, Sr, Ba), B, Al, Si, P, Ti, V, Cr, Mn, Cu, Zn, Ga, Ge, Zr, Nb, Mo, Ru, Rh, Pd, Ag, In, Sn, Sb, Te, Ta, W, Re, Os, Ir, Pt, Au, Tl, Pb, Bi, and Ce.

To promote the hydrogenation or increase the yield, the hydrogenation may be conducted in the presence of a known co-catalyst. Examples of the co-catalyst include hydroxides or alcoholates (alkoxides) of alkali metals or alkaline earth metals. The selectivity can be additively increased in some cases by the combined use of the co-catalyst.

The hydrogenation may be conducted in either a fixed bed manner or a slurry bed manner, and also in either a batch wise manner or a continuous manner. Particularly, a fixed bed, continuous flow method using a trickle bed reactor is preferred for its easiness when the hydrogenation is industrially carried out in a liquid phase. The hydrogenation temperature is preferably from 20 to 250° C., more preferably from 20 to 200° C., and the reaction pressure (hydrogen partial pressure) is preferably from 0 to 30 MPaG, more preferably from 0.2 to 20 MPaG, and still more preferably from 0.5 to 15 MPaG, although each depending upon the kinds of the catalyst and nitrile. The amount of the catalyst to be used is preferably from 0.1 to 100 parts by weight per 100 parts by weight of the raw nitrile for the slurry bed, batch wise hydrogenation, although depending upon the kinds of the catalyst and nitrile. Within the above range, the hydrogenation proceeds sufficiently and the production cost is low. In the fixed bed, continuous hydrogenation, the raw nitrile is fed at a rate of from 0.01 to 1000 parts by weight/h per 100 parts by weight of the catalyst.

In the present invention, the hydrogenation catalyst is pretreated with a specific treating agent before use in the hydrogenation of nitrile. With such a pretreatment, the side reaction which gives the condensation products is prevented, to increase the yield of the primary amine. The treating agent for the pretreatment includes hydrocarbons, natural gas, alcohols, ethers, esters and carbon monoxide.

Examples of the hydrocarbons as the treating agent include alkanes, alkenes and alkynes each having 12 or less carbon atoms, with carbon-carbon unsaturated compounds, i.e., alkenes and alkynes being preferred and alkenes being more preferred. Examples of alkanes include methane, ethane, propane, butane, pentane, hexane, heptane, and octane (inclusive of structural isomers such as isobutane and isopentane), and further include cyclopentane, cyclohexane and methylcyclohexane. Examples of alkenes include ethylene, propylene, butene, butadiene, pentene, hexene, heptene and octene (inclusive of structural isomers such as isobutene and isopentene), and further include cyclopentadiene, cyclohexene and methylcyclohexene. Examples of alkynes include acetylene, methylacetylene and ethylacetylene. Aromatic hydrocarbon such as benzene, toluene and xylene are also usable. Of the above hydrocarbons, particularly preferred are alkenes having 4 or less carbon atoms such as ethylene, propylene and butene.

The natural gas is a mixture of hydrocarbon compounds which is mainly composed of alkanes having 6 or less carbon atoms, and suitably used as the treating agent.

The alcohols as the treating agent have preferably 6 or less carbon atoms. Examples thereof include methanol, ethanol, n-propanol, isopropanol, n-butanol, isobutanol, t-butanol, ethylene glycol and ally alcohol, with methanol and ethanol being preferred and methanol being particularly preferred. The alcohols having no carbonyl group, carboxyl group and amide group are preferably used.

The ethers as the treating agent have preferably 12 or less carbon atoms, more preferably 6 or less carbon atoms. Examples thereof include dimethyl ether, diethyl ether, methyl ethyl ether, ethylene glycol monomethyl ether, and diglyme, with dimethyl ether and diethyl ether being preferred and dimethyl ether being particularly preferred. The ethers having no carbonyl group, carboxyl group and amide group are preferably used.

The ester as the treating agent is preferably a methyl ester or an ethyl ester. Examples thereof include methyl formate, methyl acetate and ethyl acetate. The esters having no carbonyl group, carboxyl group and amide group are preferably used.

The above treating agents may be used alone or in combination of two or more.

The pretreatment by the hydrocarbon, natural gas, alcohol or ether is conducted in either gas phase (vapor phase) or liquid phase, with the treatment in gas phase being preferred. The pretreatment by the ester or carbon monoxide is conducted preferably in gas phase (vapor phase).

If a catalyst which is stabilized by the treatment with oxygen or carbon dioxide is used, the stabilized catalyst may be reduced with hydrogen prior to the pretreatment.

A large amount of hydrogen in the pretreatment atmosphere may reduce the effect of pretreatment. Therefore, the pretreatment atmosphere containing hydrogen in a lower content is preferred, and the hydrogen-free atmosphere is most preferred. In the gas phase (vapor phase) pretreatment, the molar ratio of hydrogen and the treating agent (hydrogen/treating agent) in the gas phase is maintained preferably at 6 or less, more preferably at 3 or less, and particularly preferably at 1.5 or less. In the liquid phase pretreatment, the molar ratio of hydrogen and the treating agent (hydrogen/treating agent) in the atmosphere for the pretreatment is maintained preferably at 6 or less, more preferably at 3 or less, and particularly preferably at 1.5 or less. If the catalyst is brought into contact with a hydrogen-containing gas at high temperatures in the absence of the treating agent after the pretreatment, the effect of the pretreatment may be reduced in some cases. Therefore, it is preferred to cool the catalyst in the absence of hydrogen after the pretreatment, and then, use the catalyst in the hydrogenation of nitrile.

Since oxygen in the pretreatment atmosphere deactivates the catalyst, the pretreatment is conducted preferably in the absence of oxygen.

In the gas phase pretreatment, the catalyst is brought into contact with a gas (vapor) of at least one treating agent. The concentration of the treating agent in the pretreatment atmosphere may be regulated within the desired range by a diluting gas such as nitrogen, argon, helium, water vapor, carbon dioxide, and hydrogen. If the hydrogenation is conducted in a fixed bed manner, the gas containing the vapor of the treating agent is preferably passed through the catalyst bed because such a process is quite easy and a complicated operation such as solvent exchange is not needed before use in the hydrogenation of nitrile.

In the liquid-phase pretreatment, the catalyst is brought into contact with a liquid containing at lease one treating agent selected from the hydrocarbons, natural gas, alcohols and ethers. If the treating agent is gas (vapor) or solid under the pretreatment conditions, the treating agent may be dispersed or dissolved in an appropriate dispersion medium or solvent such as water and ammonia. If the hydrogenation is conducted in a slurry bed manner, the pretreatment is easily conducted by keeping the catalyst dispersed in a liquid containing the treating agent or by blowing a gas of the treating agent into a slurry of the catalyst dispersed in a dispersion medium.

The pretreatment temperature is preferably higher than the hydrogenation temperature of the nitrile, more preferably from 150 to 500° C., still more preferably from 180 to 450° C., and particularly preferably from 200 to 400° C., although depending upon the kinds of the catalyst and treating agent. Within the above ranges, a sufficient effect of the pretreatment is obtained and the reduction in the activity and selectivity can be avoided.

The pretreatment time is preferably from 5 s to 50 h, more preferably from 1 min to 40 h, and still more preferably from 5 min to 30 h, although depending upon the kinds of the catalyst and treating agent. Within the above ranges, a sufficient effect of the pretreatment is obtained and the reduction in the activity and selectivity can be avoided.

In the gas phase pretreatment, the concentration of the treating agent in the treating gas is preferably from 0.1 to 100 vol %, more preferably from 0.2 to 20 vol %, and still more preferably from 0.5 to 10 vol %. If the treating gas containing the treating agent is passed through a catalyst bed, the space velocity (GHSV) is preferably from 30 to 10000 $h^{-1}$, more preferably from 50 to 5000 $h^{-1}$, and still more preferably from 50 to 3000 $h^{-1}$.

The total amount of the treating agent to be used is preferably from 0.1 to 100 mol, more preferably from 0.2 to 50 mol, and still more preferably from 0.3 to 20 mol per 1 kg of the catalyst, although depending upon the kind of the treating agent and the pretreatment conditions such as temperature.

The pressure of the pretreatment is preferably selected from the range of atmospheric pressure to the hydrogenation pressure, more preferably from the range of from 0 to 30 MPaG. Generally, a sufficient effect is obtained under the low pressure condition of from atmospheric pressure to 1 MPaG.

Using the catalyst pretreated in the manner described above, the by-production of the condensation products such as secondary amines and tertiary amines which are produced by the intermolecular condensation during the hydrogenation of nitrile is extremely prevented, and the selectivity and yield of the primary amines is increased. By the pretreatment, the amount of the condensation products being produced is reduced by 15% or more, preferably 30% or more, and more preferably 50% or more, as compared with the hydrogenation using a catalyst not pretreated.

The present invention will be described in more detail with reference to the examples and comparative examples. However, it should be noted that the scope of the present invention is not limited to the following examples. The results of the reaction were evaluated by the analysis using a gas chromatograph equipped with a DB-1 column (Agilent (J&W) Co., Ltd.).

Preparation of Catalyst

In a solution prepared by dissolving 305.0 g of nickel nitrate hexahydrate ($Ni(NO_3)_2.6H_2O$), 6.5 g of copper nitrate trihydrate ($Cu(NO_3)_2.3H_2O$), and 7.1 g of chromium nitrate nonahydrate ($Cr(NO_3)_3.9H_2O$) in 1 kg of pure water at 40° C., 29.6 g of diatomaceous earth was suspended under stirring at 40° C. to prepare a slurry. A solution prepared by dissolving 128.6 g of sodium carbonate ($Na_2CO_3$) in 1 kg of pure water at 40° C. was added to the slurry under vigorous stirring to cause the precipitation. The resultant slurry was heated to 80° C. and maintained there for 30 min. Then, the precipitate was separated by filtration and washed. The precipitate was dried at 110° C. overnight and then calcined at 380° C. for 18 h in air. The obtained calcined powder was mixed with graphite in an amount of 3% by weight of the powder and then punched into a form of 3.0 mm φ×2.5 mm tablets. The tables were reduced at 400° C. in a hydrogen stream. The reduced tablets were oxidized overnight for stabilization at room temperature to 40° C. in a diluted oxygen gas stream (oxygen/nitrogen=1/

99 by volume). Then, the tablets were crushed and classified into 60 to 80 mesh, to obtain Catalyst A.

Comparative Example 1

A stainless reaction tube with a 4-mm inner diameter was charged with 0.2 g of Catalyst A. By allowing pure hydrogen gas to pass through the catalyst bed for 10 h under the pretreatment conditions of atmospheric pressure, 250° C., and a gas flow rate of 0.6 NL/h to reduce the catalyst for activation. The supply of hydrogen gas was stopped and the reaction tube was cooled to 50° C. Then, the inner pressure of the reaction tube was raised to 10 MPaG by hydrogen and the catalyst bed was made wet with liquid ammonia by introducing ammonia. Then, the hydrogenation was conducted in a continuous manner while supplying hydrogen gas at 0.6 NL/h and a liquid mixture of isophthalonitrile (IPN), pseudocumene (PCM) and ammonia ($NH_3$) in a weight ratio of IPN:PCM:$NH_3$=8:8:84 at 2 g/h from the upper portion of the reaction tube. The total pressure was 10 MPaG and the reaction temperature was 80° C. After 24 h of the hydrogenation, the conversion of isophthalonitrile was 100 mol %, the yield of m-xylylenediamine was 92.1 mol %, the yield of high-boiling condensation products was 7.8 mol %, and the yield of methylbenzylamine was 0.1 mol %.

Example 1

Treating Agent: Ethylene

A stainless reaction tube with a 4-mm inner diameter was charged with 0.2 g of Catalyst A. By allowing pure hydrogen gas to pass through the catalyst bed for 10 h under the conditions of atmospheric pressure, 250° C., and a flow rate of 0.6 NL/h to reduce the catalyst for activation. Then, the hydrogen gas was changed to a mixed gas (ethylene:nitrogen=4:9 by volume) and the mixed gas was allowed to pass through the catalyst bed for 1 h under the pretreatment conditions of atmospheric pressure, 250° C., and a flow rate of 0.6 NL/h, to pretreat the catalyst. The supply of the mixed gas was stopped and the reaction tube was cooled to 50° C. Then, the inner pressure of the reaction tube was raised to 10 MPaG by hydrogen and the catalyst bed was made wet with liquid ammonia by introducing ammonia. Then, the hydrogenation was conducted in a continuous manner while supplying hydrogen gas at 0.6 NL/h and a liquid mixture (IPN:PCM:$NH_3$=8:8:84 by weight) at 2 g/h from the upper portion of the reaction tube. The total pressure was 10 MPaG and the reaction temperature was 80° C. After 24 h of the hydrogenation, the conversion of isophthalonitrile was 100 mol %, the yield of m-xylylenediamine was 96.8 mol %, the yield of high-boiling condensation products was 3.1 mol %, and the yield of methylbenzylamine was 0.1 mol %.

As compared with Comparative Example 1, by pretreating the catalyst, the yield of the condensation products was reduced to less than half (from 7.8 mol % to 3.1 mol %), while the yield of the aimed primary amine (m-xylylenediamine) was correspondingly increased.

Example 2

Treating Agent: Propylene

The procedure of Example 1 was repeated except for changing the pretreatment gas to a mixed gas (propylene:nitrogen=4:96 by volume) and the pretreatment conditions to atmospheric pressure, 200° C., a flow rate of 0.025 NL/h and 3 h. After 24 h of the hydrogenation, the conversion of isophthalonitrile was 100 mol %, the yield of m-xylylenediamine was 97.8 mol %, and the yield of high-boiling condensation products was 2.1 mol %.

Example 3

Treating Agent: Propylene

The procedure of Example 1 was repeated except for changing the pretreatment gas to a mixed gas (propylene:nitrogen=4:96 by volume). After 24 h of the hydrogenation, the conversion of isophthalonitrile was 100 mol %, the yield of m-xylylenediamine was 96.3 mol %, and the yield of high-boiling condensation products was 3.7 mol %.

Example 4

Treating Agent: Natural Gas

The procedure of Example 1 was repeated except for changing the pretreatment gas to natural gas (nitrogen:carbon dioxide:methane:ethane:propane:butane:other hydrocarbons=0.16:0.58:88.69:7.07:1.79:1.19:0.52 by volume) and the pretreatment conditions to atmospheric pressure, 280° C., a flow rate of 0.6 NL/h, and 6 h. After 24 h of the hydrogenation, the conversion of isophthalonitrile was 100 mol %, the yield of m-xylylenediamine was 95.2 mol %, and the yield of high-boiling condensation products was 4.8 mol %.

Example 5

Treating Agent: Propane

The procedure of Example 1 was repeated except for changing the pretreatment gas to a mixed gas (propane:nitrogen=6:94 by volume) and the pretreatment conditions to atmospheric pressure, 250° C., a flow rate of 0.6 NL/h, and 2 h. After 24 h of the hydrogenation, the conversion of isophthalonitrile was 100 mol %, the yield of m-xylylenediamine was 95.2 mol %, and the yield of high-boiling condensation products was 4.8 mol %.

Example 6

Treating Agent: Dimethyl Ether

The procedure of Example 1 was repeated except for changing the amount of Catalyst A to 0.6 g, the pretreatment gas to a mixed gas (dimethyl ether:nitrogen=9:91 by volume), and the pretreatment conditions to atmospheric pressure, 250° C., a flow rate of 0.6 NL/h, and 2 h. After 24 h of the hydrogenation, the conversion of isophthalonitrile was 100 mol %, the yield of m-xylylenediamine was 98.3 mol %, and the yield of high-boiling condensation products was 1.7 mol %.

Example 7

Treating Agent: Methanol

The procedure of Example 1 was repeated except for changing the amount of Catalyst A to 0.6 g, the pretreatment gas to a mixed gas (methanol:nitrogen=4:96 by volume), and the pretreatment conditions to atmospheric pressure, 200° C., a flow rate of 0.18 NL/h, and 3 h. After 24 h of the hydrogenation, the conversion of isophthalonitrile was 100 mol %, the yield of m-xylylenediamine was 98.5 mol %, and the yield of high-boiling condensation products was 1.5 mol %.

Example 8

Treating Agent: Methanol

The procedure of Example 1 was repeated except for changing the amount of Catalyst A to 0.6 g, the pretreatment gas to a mixed gas (methanol:nitrogen=1:99 by volume), and the pretreatment conditions to atmospheric pressure, 280° C., a flow rate of 0.09 NL/h, and 12 h. After 24 h of the hydrogenation, the conversion of isophthalonitrile was 100 mol %, the yield of m-xylylenediamine was 98.8 mol %, and the yield of high-boiling condensation products was 1.2 mol %.

Example 9

Treating Agent: Methanol

The procedure of Example 1 was repeated except for changing the amount of Catalyst A to 0.6 g, the pretreatment gas to a mixed gas (methanol:hydrogen:nitrogen=4:11:85 by volume), and the pretreatment conditions to atmospheric pressure, 250° C., a flow rate of 0.09 NL/h, and 3 h. After 24 h of the hydrogenation, the conversion of isophthalonitrile was 100 mol %, the yield of m-xylylenediamine was 97.7 mol %, and the yield of high-boiling condensation products was 2.3 mol %.

Example 10

Treating Agent: Methanol

The procedure of Example 1 was repeated except for changing the amount of Catalyst A to 0.6 g, the pretreatment gas to a mixed gas (methanol:carbon dioxide:nitrogen=4:20:76 by volume), and the pretreatment conditions to atmospheric pressure, 250° C., a flow rate of 0.09 NL/h, and 3 h. After 24 h of the hydrogenation, the conversion of isophthalonitrile was 100 mol %, the yield of m-xylylenediamine was 99.3 mol %, and the yield of high-boiling condensation products was 0.7 mol %.

Example 11

Treating Agent: Methanol and Methane

The procedure of Example 1 was repeated except for changing the amount of Catalyst A to 0.6 g, the pretreatment gas to a mixed gas (methanol:methane:nitrogen=4:20:76 by volume), and the pretreatment conditions to atmospheric pressure, 250° C., a flow rate of 0.09 NL/h, and 3 h. After 24 h of the hydrogenation, the conversion of isophthalonitrile was 100 mol %, the yield of m-xylylenediamine was 98.6 mol %, and the yield of high-boiling condensation products was 1.4 mol %.

Example 12

Treating Agent: Methanol

The procedure of Example 1 was repeated except for using terephthalonitrile in place of isophthalonitrile and changing the amount of Catalyst A to 0.6 g, the pretreatment gas to a mixed gas (methanol:nitrogen=4:96 by volume), and the pretreatment conditions to atmospheric pressure, 250° C., a flow rate of 0.18 NL/h, and 3 h. After 24 h of the hydrogenation, the conversion of terephthalonitrile was 100 mol %, the yield of p-xylylenediamine was 98.7 mol %, and the yield of high-boiling condensation products was 1.3 mol %.

Comparative Example 2

The procedure of Example 12 was repeated except for omitting the pretreatment. After 24 h of the hydrogenation, the conversion of terephthalonitrile was 100 mol %, the yield of p-xylylenediamine was 92.4 mol %, and the yield of high-boiling condensation products was 7.6 mol %.

Example 13

Treating Agent: Methanol

The procedure of Example 12 was repeated except for using adiponitrile except for terephthalonitrile. After 24 h of the hydrogenation, the conversion of adiponitrile was 100 mol %, the yield of hexamethylenediamine was 97.0 mol %, the yield of hexamethyleneimine was 1.1 mol %, and the yield of high-boiling condensation products was 1.9 mol %.

Comparative Example 3

The procedure of Example 13 was repeated except for omitting the pretreatment. After 24 h of the hydrogenation, the conversion of adiponitrile was 100 mol %, the yield of hexamethylenediamine was 90.1 mol %, the yield of hexamethyleneimine was 1.3 mol %, and the yield of high-boiling condensation products was 8.6 mol %.

Example 14

Treating Agent: Carbon Monoxide

The procedure of Example 1 was repeated except for changing the amount of Catalyst A to 0.6 g, the pretreatment gas to a mixed gas (carbon monoxide:nitrogen=20:80 by volume), and the pretreatment conditions to atmospheric pressure, 250° C., a flow rate of 0.09 NL/h, and 3 h. After 24 h of the hydrogenation, the conversion of isophthalonitrile was 100 mol %, the yield of m-xylylenediamine was 98.9 mol %, and the yield of high-boiling condensation products was 1.1 mol %.

Example 15

Treating Agent: Methyl Formate

The procedure of Example 1 was repeated except for changing the amount of Catalyst A to 0.6 g, the pretreatment gas to a mixed gas (methyl formate:nitrogen=26:74 by volume), and the pretreatment conditions to atmospheric pressure, 250° C., a flow rate of 0.09 NL/h, and 3 h. After 24 h of the hydrogenation, the conversion of isophthalonitrile was 100 mol %, the yield of m-xylylenediamine was 95.8 mol %, and the yield of high-boiling condensation products was 4.2 mol %.

Example 16

Treating Agent: Ethylene

The procedure of Example 1 was repeated except for using 0.6 g of crushed powders (60 to 80 mesh) of a cobalt/diatomaceous earth catalyst ("G67" available from Süd-Chemie AG, cobalt content=56%) and changing the pretreatment gas to a mixed gas (ethylene:nitrogen=4:96 by volume), the pretreatment conditions to atmospheric pressure, 290° C., a flow rate of 0.18 NL/h, and 3 h, and the hydrogenation temperature to 100° C. After 50 h of the hydrogenation, the conversion of isophthalonitrile was 100 mol %, the yield of m-xylylenediamine was 96.2 mol %, and the yield of high-boiling condensation products was 3.8 mol %.

Comparative Example 4

The procedure of Example 16 was repeated except for omitting the pretreatment. After 50 h of the hydrogenation, the conversion of isophthalonitrile was 100 mol %, the yield of m-xylylenediamine was 94.0 mol %, and the yield of high-boiling condensation products was 6.0 mol %.

Comparative Example 5

Into a 300-ml SUS autoclave equipped with a stirrer, 10 g of isophthalonitrile was charged. Then, a slurry prepared by dispersing 3 g of a leached sponge nickel catalyst ("NDHT" available from Kawaken Fine Chemicals Co., Ltd.) in 60 g of methanol was charged and the autoclave was closed. After replacing the air in the autoclave with nitrogen, 30 g of ammonia was charged. The inner pressure was raised to 5 MPaG by hydrogen, and the hydrogenation was allowed to proceed at 65° C. The pressure was maintained at 5 MPaG by introducing hydrogen to supplement the consumed hydrogen. After 4 h of the hydrogenation, a part of the reaction liquid was sampled and analyzed. The conversion of isophthalonitrile was 100 mol %, the yield of m-xylylenediamine was 84.8 mol %, the yield of 3-cyanobenzylamine was 0.2 mol %, and the yield of high-boiling condensation products was 15 mol %.

Example 17

Treating Agent: Methanol

The same type of sponge nickel catalyst as used in Comparative Example 5 was charged into a glass tube with a 10-mm inner diameter in an amount of 3 g and dried at 200° C. in a nitrogen stream. Then, a mixed gas (methanol:nitrogen=4:96 by volume) was allowed to pass through the catalyst bed to pretreat the catalyst under the conditions of atmospheric pressure, 200° C., a flow rate of 1.5 NL/h, and 3 h. After the pretreatment, the catalyst was cooled to 30° C. in a nitrogen gas flow. The pretreated catalyst was slurried in 60 g of methanol in a nitrogen atmosphere. The hydrogenation of isophthalonitrile was conducted in the same manner as in Comparative Example 5 except for using the pretreated catalyst thus prepared. After 4 h of the hydrogenation, a part of the reaction liquid was sampled and analyzed. The conversion of isophthalonitrile was 100 mol %, the yield of m-xylylenediamine was 92.8 mol %, the yield of 3-cyanobenzylamine was 0.2 mol %, and the yield of high-boiling condensation products was 7 mol %.

As described above, by conducting the hydrogenation of nitrile in the presence of a catalyst which is pretreated with a specific treating agent, the amount of the by-produced condensation products is extremely reduced and the yield of the aimed primary amine is increased. Since the procedure of the pretreatment is very simple, the pretreated catalyst is used in the hydrogenation of nitrile in industrial scale immediately after the pretreatment without needing complicated operation. In addition, the pretreatment is effected by using easily available and inexpensive treating agents such as methanol, dimethyl ether, ethylene and natural gas. Therefore, the present invention is of great industrial value.

The primary amines produced by the method of the present invention are industrially useful as the raw materials for polyamide resins, epoxy curing agents, etc. and the intermediate raw materials for isocyanates, organic solvents, agricultural chemicals, medicines, detergents, etc.

What is claimed is:

1. A catalyst for producing a primary amine by a hydrogenation of nitrile, which comprises at least one metal selected from the group consisting of nickel, cobalt and iron, and which is modified by a pretreatment with at least one treating agent selected from the group consisting of hydrocarbons, natural gas, alcohols, ethers and esters at 180 to 500° C.

2. The catalyst according to claim 1, which is modified by the pretreatment in a gas phase with at least one treating agent selected from the group consisting of hydrocarbons, natural gas, alcohols, ethers, and esters.

3. The catalyst according to claim 1, which is modified by the pretreatment in a liquid phase with at least one treating agent selected from the group consisting of hydrocarbons, natural gas, alcohols and ethers.

4. The catalyst according to claim 1, wherein said pretreatment is at a temperature in a range of 180 to 450° C.

5. The catalyst according to claim 1, wherein said pretreatment is at a temperature in a range of 200 to 400° C.

6. The catalyst according to claim 1, wherein said at least one metal includes nickel.

7. The catalyst according to claim 1, wherein said at least one metal is selected from the group consisting of nickel and cobalt.

8. The catalyst according to claim 1, wherein the pretreatment is performed in the presence of nitrogen gas in addition to said at least one treating agent.

9. The catalyst according to claim 1, wherein a pretreatment time for said pretreatment is in a range of 5 sec to 50 hrs.

10. The catalyst according to claim 1, wherein the pretreatment is conducted in a hydrogen-free atmosphere.

11. The catalyst according to claim 1, wherein the pretreatment is conducted with a molar ratio of hydrogen to the treating agent (hydrogen/treating agent), in the atmosphere for pretreatment, of 6 or less.

* * * * *